United States Patent [19]

Marks, Sr. et al.

[11] 4,434,181

[45] Feb. 28, 1984

[54] TEAT DIP

[75] Inventors: George B. Marks, Sr., Hudson, Wis.; D. Michael Fearing, St. Paul, Minn.

[73] Assignee: Fearing Manufacturing Co., Inc., St. Paul, Minn.

[21] Appl. No.: 427,741

[22] Filed: Sep. 29, 1982

Related U.S. Application Data

[63] Continuation-in-part of Ser. No. 327,795, Dec. 7, 1981, abandoned.

[51] Int. Cl.$^3$ .................... A61K 31/155; A61K 47/00
[52] U.S. Cl. ..................................... 424/326; 424/362
[58] Field of Search ................. 424/80, 329, 303, 362, 424/326

[56] References Cited

U.S. PATENT DOCUMENTS 3,485,915  12/1969  Gerstein et al. .................... 424/362
4,193,989  3/1980   Teng et al. ......................... 424/362
4,199,564  4/1980   Silver et al. ......................... 424/80

OTHER PUBLICATIONS

Godinho–Chem. Abst., vol. 94, (1981), p. 97809x.

Primary Examiner—Sam Rosen
Attorney, Agent, or Firm—Jacobson & Johnson

[57] ABSTRACT

A method and composition for the prevention of mastitis in animals. The composition comprises a water soluble film former such as hydroxypropyl cellulose, ethyl cellulose and methyl cellulose, and chlorhexidine (preferably as the gluconate), carried in a freeze-resistant, rapidly evaporating solvent comprising a volatile alcohol. When animal teats are dipped into the composition, a liquid film containing chlorhexidine remains on the teats, and the liquid vehicle quickly evaporates to form a protective film that coats the teats to prevent bacterial infection.

8 Claims, No Drawings

TEAT DIP

RELATED APPLICATION

This is a continuation-in-part of our copending application titled "Teat Dip", U.S. Ser. No. 327,795, filed Dec. 7, 1981, now abandoned.

BACKGROUND OF THE INVENTION

1. Field of the Invention

This invention relates generally to treatment of animal udders to prevent bacterial infection such as mastitis.

2. Description of the Prior Art

The concept of teat treatment to prevent mastitis by application of a physical barrier such as a film-forming polymer latex is old in the art as evidenced by the Andrews, et al. U.S. Pat. No. 4,113,854. The Andrews patent discloses a method for the prevention of mastitis in milk-producing animals in which the teats of the animal are dipped into a solution which is comprised of a film-forming polymer latex and a water soluble polymer thickening agent in an aqueous medium. In addition, the Andrews U.S. Pat. No. 4,113,854 in column 1, lines 43 to 63 describes the prior film-forming materials containing polyvinyl acetate and polyvinyl chloride or vegetable oils which Andrews found to either be ineffective or to produce irritation to the animal's teat.

Andrews states his solution should have a thioxotropic value of 15 to 1200 dynes/cm$^2$ and a practical upper viscosity limit of 10 poise at a shear rate of 250/sec. Andrews suggests natural or synthetic water soluble polymers which include the modified polymers which are derivatives of cellulose. Andrews points out that cellulose is not water soluble without modification and states that typical cellulose derivatives include methyl, hydroxyethyl and sodium carboxymethyl cellulose derivatives and combinations thereof. Andrews also requires a polymer latex which has suitable film-forming characteristics. The latexes of styrene butadiene, acrylic polymers and acrylic copolymers. He states the preferred polymer latexes include ethyl acrylate/methyl methacrylate copolymers, methyl methacrylate/butyl acrylate copolymers and styrene butadiene copolymers. An especially preferred material of Andrews is an ethyl acrylate/methyl methacrylate copolymer.

In addition, Andrews suggests adding an antiseptic material such as alcohol, chlorohexidine, iodine, 8-hydroxy quinoline sulfate or sodium hypochlorite to his mixture.

Andrews contends that when the teat is dipped in the mixture, it forms a film around the animal's teat which provides a shield against bacterial infections such as mastitis.

One of the problems with the prior art teat coating is that although the Andrews patent describes such teat coating as water soluble, in practice it has been difficult to completely remove the film barriers on the teat with water which may result in plugging the milk line filters. The sales literature of Andrews' assignee, Minnesota Mining and Manufacturing Company, titled *The Physical Barrier Against Mastitis*, alludes to the problem of incomplete removal by stating "Teat shield will not dissolve in milk. Your filter will trap any entering the milk line."

While Andrews emphasizes the physical barrier aspect of a film formed by the combination of polymer latex and a water soluble thickening agent, he also suggests one could incorporate an antiseptic into the material. One of the problems is to provide a workable combination of film and antiseptic that do not react with each other. We have discovered that the combination of chlorhexidine (typically as the gluconate) and a water soluble cellulosic film-former, typically hydroxmethyl cellulose, provides a film that provides long lasting bacterial protection to an animal's teats.

One of the problems associated with prior art teat dips is that during storage the teat dip solution may freeze and separate. The present invention overcomes this problem by use of an alcohol solution which does not freeze under normal barn storage temperatures, e.g., temperatures down to minus 18° C. or thereabouts, but below 0° C. The alcohol readily evaporates when placed on the cow's teat to permit the film to rapidly form on the animal's teat.

Still other prior art is described in the *Journal of American Veterinary Medical Association* article of Farnsworth, Wyman and Hawkinson titled "Use of a Teat Sealer for Prevention of Intramammary Infections in Lactating Cows". This article describes the use of an acrylic latex film as a physical barrier which is removed by rubbing.

The prior art also shows the use of nonfilm-forming teat dips marketed under the trade name Tesan. The Tesan dip comprises a liquid solution and bactericide of chlorhexidine which is claimed to adhere to the animal's teats.

Another teat dip is described in the product bulletin of Lonze Technical Service Laboratories. Lonza's product uses chlorhexidine gluconate in combination with other ingredients. The Lonza product is also a nonfilm-forming coating.

Still other publications such as the *Journal of Dairy Science* lists a number of germicides for use in teat dip preparation.

The present invention comprises an improvement to the prior art teat dips by providing a film-forming liquid that is safe and can be completely removed with water.

SUMMARY OF THE INVENTION

The present invention is directed to the discovery of a teat dip composition containing a cellulosic film former (typically hydroxypropyl cellulose) and an antiseptic such as chlorhexidine (typically as the gluconate) in a liquid vehicle including a volatile alcohol. The composition provides a rapidly drying film barrier on animal teats that can easily be removed with water. The composition is resistant to freezing.

DESCRIPTION OF THE PREFERRED EMBODIMENT

The solution of the present invention is characterized as a liquid at room temperature in which one can immerse an animal teat to provide a liquid coating that adheres to the animal's teat. As the liquid vehicle of the coating evaporates, the coating congeals to form a clear film barrier located on the outside of the teat. In order to kill bacteria and prevent mastitis spreading, it is preferred to have an antiseptic material such as chlorhexidine in the film to kill bacteria and prevent bacteria from entering the milk gland in the teat. In the present invention one prepares a solution of a film-forming cellulose derivative such as hydroxypropyl cellulose in a solution comprising a volatile alcohol. To provide added mastitis protection one adds an antiseptic material such as chlorhexidine gluconate to the solution. The alcohol in the solution provides for rapid evaporation while the hydroxypropyl cellulose forms a physical film barrier around the teat. When it is time to milk the animal, the film on the teat can be thoroughly and completely removed with water.

Examples of the preparation of the solution of the present invention are as follows:

EXAMPLE I

Five parts by weight chlorhexidine gluconate were mixed with 15 parts by weight of hydroxypropyl cellulose and 80 parts by weight of isopropyl alcohol at room temperature (70° F.). The resulting mixture, although liquid, exhibited thixotropy and had characteristics of a light gel solution.

EXAMPLE II

Five parts by weight of chlorhexidine gluconate were mixed with 40 parts by weight of water. The water and chlorhexidine gluconate were mixed together at room temperature (70° F.). Next, 15 parts by weight of hydroxpropyl cellulose were mixed with 40 parts by weight of isopropyl alcohol at room temperature. The resulting solutions were then mixed together at room temperature.

An animal teat to be treated was dipped in the light gel solution of the above examples. After removing the teat from the solution there remained a liquid solution of approximately 2-4 mils thickness on the teat. In a few seconds after removal of the teat from the teat dip solution the alcohol in the mixture evaporated leaving a continuous film over the teat.

The solution, which was applied after milking, produced a film coating that remained in the animal teat for approximately eight hours. The film was then washed off by hosing down the teats with water. The washing action completely removed the film with no observable residual patches of film on the teat. After repeated testing, no mastitis infection or mastitis spreading was observed in the test animals.

It should be understood that alcohol provides a rapid evaporation solvent that allow the liquid film to quickly form into a durable coating as the alcohol evaporates. Another benefit of the alcohol is that it prevents the unused teat dip solution from freezing in the winter time. Such water as may be in the solution functions to dilute the cellulose material into a light, pourable, gel form as well as acting as a carrier to disperse the antiseptic material throughout the mixture.

The liquid vehicle in which the antiseptic material and the water soluble cellulose derived film-former is employed preferably includes from about 80% to about 100% by weight of volatile alcohol. The liquid vehicle may include quantities of water ranging from very small amounts up to about 50% by weight of the liquid vehicle. When a teat has been dipped in the teat dip composition, the volatile, low-boiling alcohol constituent evaporates readily, leaving a film on the teat. If significant quantities of water, for example, 50% by weight of the liquid vehicle, are incorporated in the liquid vehicle, then the drying of the film appears to proceed in two stages. First, the majority of the volatile alcohol moiety evaporates, leaving a soft, tacky residual film on the teat. A secondary, somewhat more lengthy drying of the coating renders the coating substantially dry to the touch. If, on the other hand, the vehicle comprises primarily a volatile alcohol such as isopropanol (at least about 80% by weight), then, upon evaporation of the alcohol portion of the liquid vehicle, the coating itself becomes substantially dry to the touch even though it may contain a substantial quantity of water. In one embodiment, in which substantially the entire liquid vehicle is volatile alcohol, evaporation of the vehicle from the coating occurs quickly—within about five minutes—and the resulting coating is dry to the touch and is soft and pliable. It is believed that the film former absorbs some water from the air. Preferably, the liquid vehicle includes a sufficient concentration of volatile alcohol so that when the alcohol moiety evaporates, the film is rendered substantially dry to the touch.

The composition of the invention generally takes the form of a lightly viscous, pourable liquid. It is believed that some light gel formation occurs due to the presence of the cellulosic film former. Of interest, higher temperatures appear to increase rather than decrease the viscosity of the composition. Accordingly, when the composition is applied to warm teats, the composition tends to solidify on the teats rather quickly. The viscosity of the teat dip can be controlled through judicious selection of the type and quantity of cellulosic film former, and also through the addition of various thickening agents such as fumed silica (e.g., Cab-o-Sil, a product of Cabot Chemical Company).

Under most milking parlor conditions the preferred range of the film-forming, water soluble cellulosic material, typically hydroxypropyl cellulose, in the solution varies from a minimum of approximately 10% by weight to a maximum of approximately 20% by weight depending on the thickness of the coating desired. If the concentration of hydroxypropyl cellulose is very low, it produces a thin film coating which may easily break or rupture or even be incompletely applied to the animal's teat. On the other hand, if the mixture is too thick, i.e., concentrations of hydroxypropyl cellulose are greater than 20% by weight, it is difficult to apply the mixture to the teat as one cannot obtain a uniform coating over the teat. Thus, the range of hydroxypropyl cellulose has as its limit the practical range at which it can be applied to the animals' teat which may vary under various environmental conditions. However, it has been found the preferred amount of hydroxpropyl cellulose for most applications ranges from a minimum of 10% by weight to a maximum of 20% by weight. Under most milking parlor conditions a solution of approximately 15% by weight produces a film of sufficient durability to last from milking to milking.

The amounts of the bactericide are such that they should be effective over at least an eight hour period. While more or less bactericide can be used, the preferred range of chlorhexidine as the bactericide is a maximum of approximately 20% by weight. It should be understood that other bactericides may be used at greater or lesser concentrations; however, it has been found that chlorhexidine gluconate is ideally suited since it can be retained in the film to provide long lasting antiseptic action. If desired, the hydroxypropyl cellulose can be used without the bactericide, but the mastitis prevention that is afforded is then limited to the physical barrier effects of the film.

While hydroxypropyl cellulose is the preferred material, other cellulosic film formers such as ethyl cellulose or methyl cellulose may also be used.

We claim:

1. A liquid teat dip composition having a freezing point not less than about −5° C. and capable, upon application to the teats of an animal, of quickly forming a soft, flexible coating that is substantially dry to the touch and that can readily be washed from the teats by water washing, comprising an effective quantity of a chlorhexidine antiseptic, a water-soluble film-former derived from cellulose in an amount ranging from about 10% to about 20% by weight of the composition, and a liquid vehicle including a volatile alcohol in an amount not less than about 80% by weight of the composition.

2. The composition of claim 1 wherein the chlorhexidene antiseptic is chlorhexidene gluconate.

3. The composition of claim 1 in which the volatile alcohol is isopropanol.

4. The composition of claim 1 wherein the film-former is hydroxypropyl cellulose.

5. The composition of claim 1 wherein the liquid vehicle is a volatile alcohol, and wherein the proportions of film-former and liquid vehicle are so chosen as to provide a soft, flexible coating that is dry to the touch within about five minutes of application of the composition to teats of an animal.

6. A liquid teat dip composition having a freezing point not greater than about −5° C. and capable, upon application to the teats of an animal, of quickly forming a soft, flexible coating that is substantially dry to the touch and that can readily be washed from the teats by water washing, comprising an effective quantity of a chlorhexidene antiseptic, from about 10% to about 20%, by weight of the composition, of hydroxypropyl cellulose, and a liquid vehicle that includes a volatile alcohol in sufficient amount, but not in an amount less than about 80% by weight of the composition, to cause a film formed from the composition upon the teats of an animal to become dry to the touch within about five minutes of application of the composition.

7. The composition of claim 6 in which the antiseptic is chlorhexidene gluconate.

8. The composition of claim 6 in which the liquid vehicle is isopropanol.

* * * * *